United States Patent [19]

Reed et al.

[11] 4,218,707

[45] Aug. 19, 1980

[54] THERMOGRAPHIC AREAMETER

[75] Inventors: Lloyd D. Reed, Richmond Hill; M. Ross Howat, Islington; John E. Ulrichsen, Willowdale, all of Canada

[73] Assignee: Her Majesty the Queen in right of Canada, as represented by the Minister of National Defence, Ottawa, Canada

[21] Appl. No.: 895,068

[22] Filed: Apr. 10, 1978

[30] Foreign Application Priority Data

May 13, 1977 [CA] Canada ................ 278419

[51] Int. Cl.² .............. H04N 7/33; H04N 7/18; G01K 7/04
[52] U.S. Cl. .............. 358/113; 250/334; 128/736; 364/414; 364/415; 364/557; 358/107; 340/722; 340/753
[58] Field of Search .............. 358/110, 111, 113; 250/330, 334; 128/736, 804; 356/51; 364/414, 415, 481, 557; 340/722, 753

[56] References Cited

U.S. PATENT DOCUMENTS

| 3,580,997 | 5/1971 | Webb et al. | 358/111 |
| 3,924,130 | 12/1975 | Cohen et al. | 358/108 |
| 3,930,045 | 2/1969 | Björk et al. | 358/113 |
| 3,931,462 | 1/1976 | Extom | 358/108 |
| 3,935,382 | 1/1976 | Hunt | 358/113 |
| 4,107,735 | 8/1978 | Frohbach | 358/84 |
| 4,114,442 | 9/1978 | Pratt | 364/557 |

Primary Examiner—Robert L. Griffin
Assistant Examiner—Edward L. Coles
Attorney, Agent, or Firm—Stevens, Davis, Miller & Mosher

[57] ABSTRACT

An area meter for a thermographic display comprising means for defining a predetermined area within a scan field and means for determining and displaying a numerical representation of the proportional area of said predetermined area relative to the total area of the scan field. This is useful in the medical diagnostic field for determining with increased accuracy areas of the body which contain distinct temperature variances from the general background field.

18 Claims, 3 Drawing Figures

THERMOGRAPHIC AREAMETER

This invention relates to a system for quantizing the regions between isotherms in a thermographic television system as a fraction or percentage of the complete thermographic scan field.

BACKGROUND OF THE INVENTION

Thermographic television systems utilize the infrared electromagnetic radiation emanating from the surface of objects or bodies to form a video image. Various infrared video signals are usually displayed either in various shades of grey or in different colours, depending on whether the television display monitor provides black and white or colour displays. Consequently the surface flux variations are easily discernable by the viewer. The regions between various isotherms are normally given a distinct grey shade or colour.

Thermographic television systems have been used in applications such as crop surveying from earth satellites, in medicine, etc. Particularly in the latter application, sources of heat such as cancer nodules located deep in the body are sometimes too difficult to detect and locate distinctly and accurately due to diffusion of heat through layers of body tissue. In particular, there may be small but distinctive asymmetry of heat generation localities on opposite sides of the body, which are very difficult to discern, but which may be important.

SUMMARY OF THE INVENTION

The present invention provides a thermographic area meter which is useable in combination with a thermographic television system to quantize, as a percentage of total area, areas of the thermographic display which correspond to distinct flux or temperature ranges. Using the digital display, the user can determine with increased accuracy areas of the body which contain distinct flux or temperature variances from the general background field. Consequently particularly in breast thermography, general body scanning and stroke screening applications (in the field of medicine), a tool has now been provided which can help improve accuracy of diagnosis. The general principles however, can be used in conjunction with isotherm video displays outside the specific thermographic application described in detail herein.

The invention in general is an area meter for a thermographic display comprising means for defining a predetermined area (including, i.e. a group of areas) within a scan field and means for determining and displaying a numerical representation of the proportional area of the predetermined area relative to the total area of the scan field. The predetermined area corresponds to regions between predetermined temperature isotherms within a video thermographic scan field.

More particularly, the invention is an area meter for a video scan field comprised of means for receiving horizontal and vertical synchronization signals of a video scan field, means for receiving sample slice signals corresponding to various display windows from video display circuitry synchronized with the synchronization signals and means for selecting slice signals corresponding to a particular portion of the field and for providing a pulse signal during the period of each selected slice signal. Summing integration circuitry provides an output ramp signal integrated and increasing during the period between a pair of vertical synchronization signals and during the intervals between horizontal synchronization signals, and in the presence of the aforenoted pulse signal. The highest ramp level voltage achieved within one vertical field period is displayed on a volt-meter, which is preferably scaled to be read as a digital numerical percent figure.

The term "isotherm" is defined as a line on the screen of the monitor which traces the location of a single temperature. The areas between isotherms are therefore regions which correspond to predetermined temperature ranges. One useful display, as an example, may show isotherms at one degree intervals.

BRIEF DESCRIPTION OF THE DRAWINGS

A better understanding of this invention will be obtained by reference to the detailed description below, and to the following drawings, in which.

DETAILED DESCRIPTION OF THE PREFERRED EMBODIMENT

Figure 1:
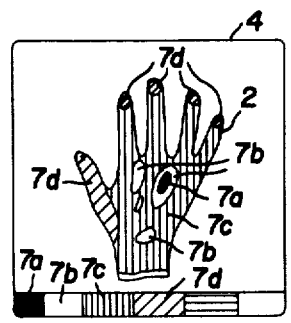
FIG. 1 depicts an example of a scan field of a video display used in a thermographic television system.
Figure 2:
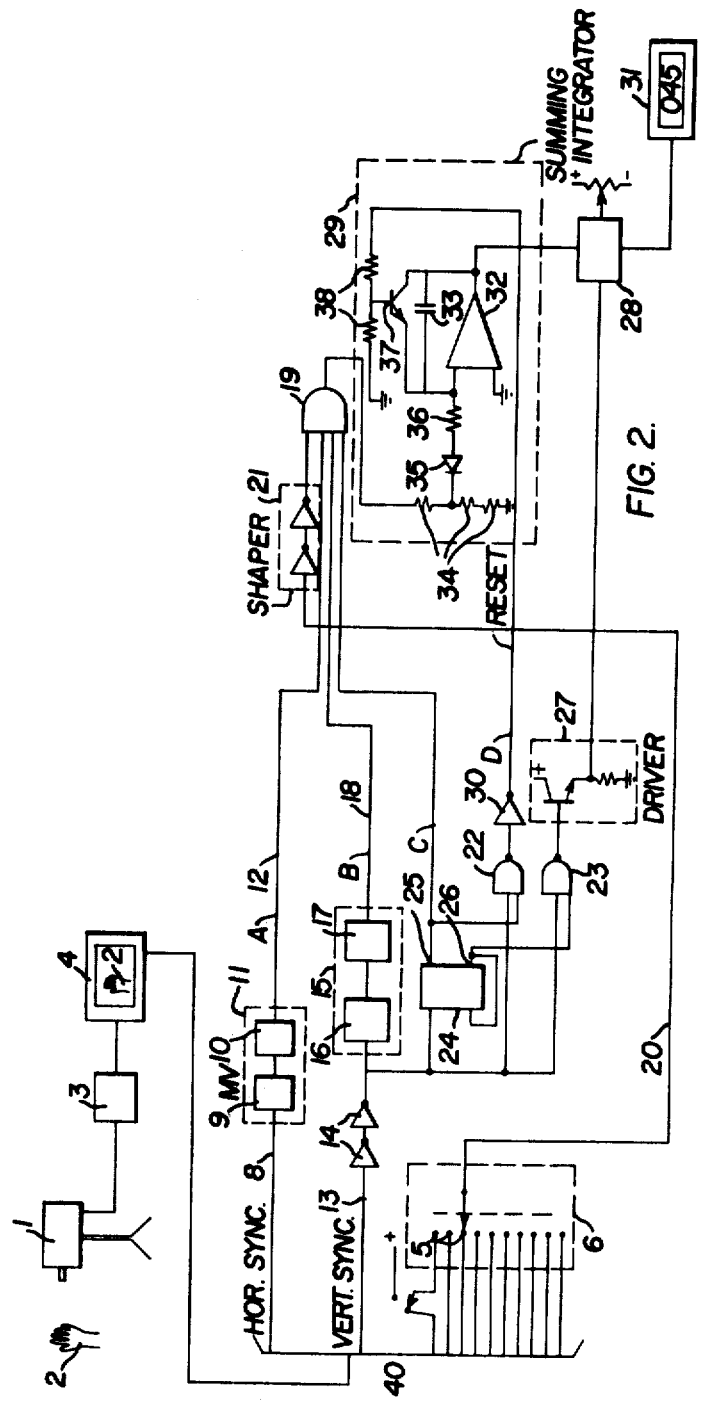
FIG. 2 is a partly block and partly detailed schematic diagram of the invention.

Turning first to FIG. 1 and the upper portion of FIG. 2, a video camera 1 which is sensitive to infrared radiation is pointed at an object such as a hand for the production of a thermographic video display. The camera output is connected to video processing circuitry 3, which is connected to a video monitor 4, which displays by means of a scanning field a thermographic representation of the subject hand 2.

The system so far described is well known and preferably is the type available from AGA of Sweden, as system 680 Thermovision Display, the colour video monitor being manufactured by Colorado Video, Inc. of the U.S.A. This apparatus is capable of displaying simultaneously ten isotherms as noted earlier, with a colour video monitor used to display the isotherms using a different colour between each isotherm. The system can display the following set of isotherm ranges, separated by ten isotherms, for example:

29° to 30° C.
30° to 31° C.
31° to 32° C.
32° to 33° C.
33° to 34° C.
34° to 35° C.
35° to 36° C.
36° to 37° C.
37° to 38° C.
38° to 39° C.
above 40° C.

The video monitor 4 contains a "slicer" circuit which operates a color selection circuit so as to cause the video monitor to display predetermined colors between various isotherms. The slicer circuit operates in response to various amplitude infrared input signals received from the infrared video camera and provides an output "slicer signal" at respective terminals of a "remote indicate out" socket, while the display is presenting particular isotherms. For instance, for each of the isotherm ranges noted above, while the display is processing signals within the individual ranges, signals are present at respective corresponding terminals. This aspect being prior art, and providing the signals on which the present invention operates, it will not be described in more detail here. In the present invention, however, a plug is connected to the "remote indicate out" socket, which has its terminals connected to the terminals 5 of an isotherm selection switch 6, as shown in FIG. 2. Also, sources of horizontal and vertical synchronization pulses from the video monitor are connected to terminals of the plug in a well known manner, for use in the present invention.

As will be noted in the display depicted in FIG. 1, the hand 2 shown is displayed in various colours or shades of grey, as an example. The region 7a, shown in most dense cross-hatch is located at the hottest part of the hand, within a peripheral isotherm, while the surrounding region 7b, with other regions of the hand, are designative of a cooler temperature range. Most of the hand, shown in a different cross-hatch pattern 7c is of a third, cooler temperature gradient, while other regions 7d depict still cooler regions. It is believed clear that the video display provides an effective subjectively interpretive depiction of the temperature graduations of the subject hand.

At the bottom of the video monitor display is a bar or chart of grey scale or colour graduations which can be used to interpret the various temperature regions of the hand or other displayed body. It is the task of the present invention to provide a numerical representation of selected regions between isotherms as a percentage of the entire field, or of a portion of the field, while excluding extraneous matter such as the color or grey scale chart displayed at the bottom of the screen.

Figure 3:
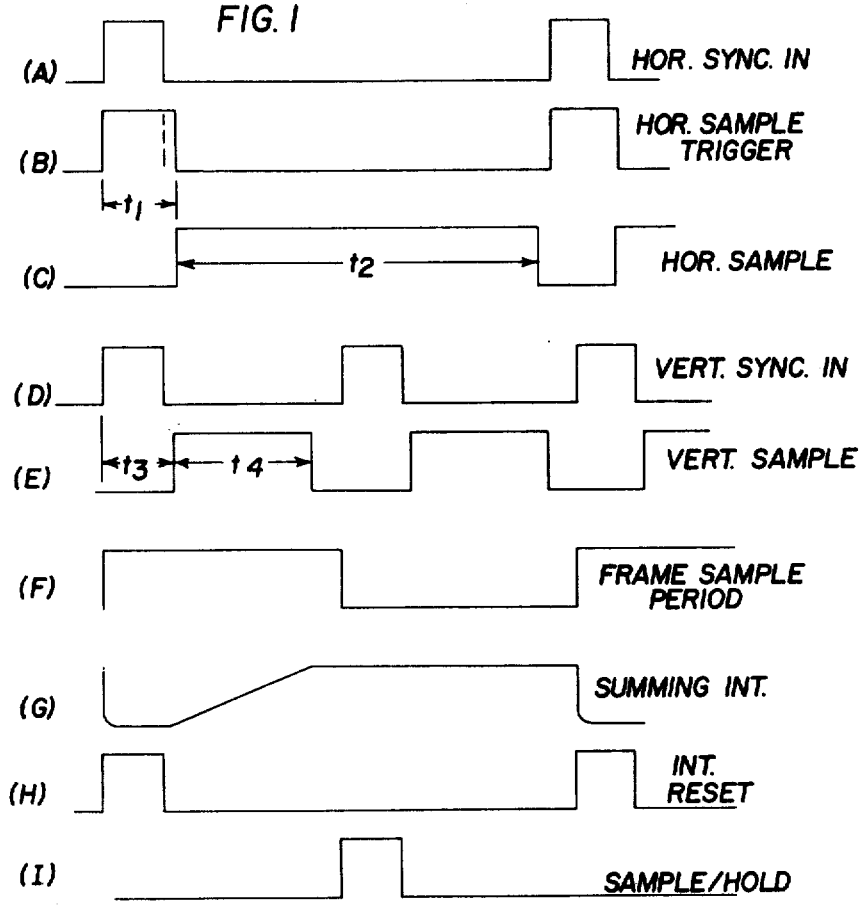
FIG. 3 is a waveform diagram showing signals at various locations in the circuitry of the apparatus.

Turning now to FIGS. 2 and 3, horizontal synchronization pulses derived from the video monitor 4 as noted above are provided on input lead 8. The horizontal synchronization pulses are depicted in FIG. 3 as waveform (A). These pulses are applied from input lead 8 to a series of two monostable multivibrators 9 and 10 which are contained within a line time definition circuit 11. The beginning of a horizontal sync pulse operates multivibrator 9, which resets after a predetermined time $t_1$ shown as part of waveform (B). At that point, the second multivibrator 10 operates, providing an output signal on its output lead 12 for a time period $t_2$ shown as part of waveform (C), after which it resets to its normal state. The time $t_2$, beginning after the end of the horizontal sync pulse and ending prior to the beginning of the next, defines the line width of the field within which sampling is taken for the purpose of the aforenoted field percentage calculation. The width of the field can therefore be varied by varying the operate times of multivibrators 9 and 10, multivibrator 9 controlling the left hand or starting point of the field and multivibrator 10 controlling the right hand or ending point. The output signal from multivibrator 10 is applied to lead 12 and is of the form of waveform (C).

In a similar manner, the vertical synchronization pulse is obtained from the video monitor 4, and is applied to input lead 13. The vertical synchronization pulse is applied to a series pair of inverters 14 which act as level detectors and eliminate any offset voltage affecting the vertical synchronization pulse. Of course, a similar shaper may be used in the horizontal input lead, if necessary.

The output signal from the inverters 14 is applied to frame time definition circuit 15, which is comprised of the series of multivibrators 16 and 17. Multivibrators 16 and 17 operate in a similar manner as multivibrators 9 and 10, and define the vertical upper and lower time limits of each frame. Waveform (D) shows the vertical synchronization pulse waveforms received from inverters 14. Multivibrator 16 operates a time $t_3$ after the beginning of a vertical synchronization pulse to define the upper limit or beginning of the frame sample period and a time $t_4$ following that period multivibrator 15 shuts off, terminating or defining the lower edge of the frame sample period, as shown in waveform (E). The time period $t_4$ depicts the vertical frame sample period, and the corresponding signal is applied to lead 18. Clearly, the time limit which defines the lower edge of the screen for sampling purposes would be set such that it does not include the time of scanning the scale definition bar at the bottom of the screen, shown in FIG. 1.

It should be noted that with external controls controlling the period of operation of multivibrators 9, 10, 16 and 17 in a well known manner, the defined field which is sampled can be placed at any rectangular area of the entire scan field. Consequently its size and location can be adjusted for diagnostic purposes. With the addition of suitable circuitry, if the time of operation of the multivibrators are made variable relative to each other, areas other than rectangular areas can be sampled, such as circular, oval, or other areas. Further, the region sampled could be intensified on the monitor screen while its boundaries are being defined.

The output lead 18 of multivibrator 17 as well as output lead 12 of multivibrator 10 are connected to individual inputs of four input NAND gate 19, which as is well known, will not operate until high level signals are present at each of its four inputs.

Turning now to switch 6, as noted earlier each of the terminals 5 has applied to it a signal during the time period between individual isotherms. A particular isotherm gradient can be selected by selecting a particular terminal 5. Consequently a signal will be present on lead 20 of switch 5 only when the selected isotherm is being processed by the video processing circuitry and is presented on the screen of video monitor 4. This isotherm gradient signal on lead 20 is applied to shaper circuit 21, which is a series pair of inverters operated similarly to inverters 14, as a level detector and offset voltage remover. The output of shaper 21 is applied to a third input of NAND gate 19.

The vertical synchronization pulse output of the shaper from inverters 14 is applied to one of the two inputs of a pair of NAND gates 22 and 23. These NAND gates will of course not be operated until there is a high level signal at the other of their inputs. The signal at the output of inverters 14 is also applied to the "clock" input of flip flop 24. One of the outputs 25 of flip flop 24 is connected to the fourth input of NAND gate 19 as well as the second input of NAND gate 22 and provides a signal thereto during the high level period in waveform F, for the time period between the leading edge of alternate vertical synchronization pulses. The second output 26 is connected both to the data input of flip flop 24 and to the second input of NAND gate 23. The output of NAND gate 23 is connected to a conventional driver circuit 27, here shown as a transistor emitter follower amplifier, which has its output connected to the enable input of a sample and hold circuit 28.

The output of NAND gate 19 is connected to a summing integrator circuit 29, which has its reset input connected to the output of NAND gate 22 through an inverting amplifier 30. The output of summing integrator 29 is connected to the signal input of sample and hold circuit 28. The output of sample and hold circuit 28 is connected to a numerical display, such as a digital volt meter 31.

The summing integrator can be of conventional form, but is preferred to be made up of a standard operational amplifier 32, having an integrating capacitor 33 connected between its output and its signal input. The output of NAND gate 19 is applied through a resistance voltage divider 34, the output of which is connected through a diode 35 and an input resistor 36 to the input of operational amplifier 32.

The collector-emitter circuit of a transistor switch 37 is connected across capacitor 33. The output of inverter amplifier 30 is connected through a resistance voltage divider 38 to the base or trigger input of transistor switch 37.

It may be seen that when the output of inverter amplifier 30 goes to high positive level, transistor switch 37 will become saturated. This provides an effective short circuit across the terminals of capacitor 33, causing it to lose its stored charge. Consequently the reset function of NAND gate 22 causes the ramp voltage level stored on capacitor 33 in conjunction with operation amplifier 32 to revert to zero.

In operation, a horizontal synchronization pulse arriving at the line time definition circuit 11 causes generation of a pulse on the output lead 12 during the time $t_2$, as described earlier and shown on waveform (C). Similarly, the frame time definition circuit 15, operating in a manner similar to the horizontal line time definition circuit is responsive to vertical synchronization pulses and will provide signal pulses on output lead 18 during period $t_4$ shown on waveform (E) which period is delayed from the beginning of a vertical synchronization pulse by the time $t_3$. Consequently the line sampling period $t_2$ and frame sampling period $t_4$ are established and defined by the pulse periods of signals applied to respective inputs of NAND gate 19.

An isotherm gradient signal which is to be measured, is selected by switch 6 and as a result appears on lead 20 during the period of that signal. This signal is processed through shaper 21 to a pulse shape and is applied to a third input of NAND gate 19.

The circuitry now to be described establishes a time for the establishment of a ramp signal, the amplitude of which is dependent on the time of operation of NAND gate 19. During a subsequent period, the voltage level of the ramp is sampled and displayed.

The vertical synchronization pulse is applied to the clock input of flip flop 24, which provides a set output on lead 25 to a fourth input of NAND gate 19, during the high level portion shown in waveform (F) as described earlier. The second output 26 of flip flop 24 is at low level during this period, inhibiting the operation of NAND gate 23. Accordingly, with all high level inputs applied to NAND gate 19, an output signal from NAND gate 19 is applied to summing integrator 29.

At the same time that the output signal of flip flop 25 is applied to an input of NAND gate 19, it is also applied to the second input of NAND gate 22, which provides an output to inverter 30. The high level output is then converted to a low level input, and the summing integrator is not reset at this interval. Consequently the summing integrator integrates the input signal arriving from NAND gate 19, and a ramp signal is produced at its output, which is connected to sample and hold circuit 28.

When the next vertical synchronization pulse arrives, and is applied to the clock input of flip flop 24, the flip flop is caused to change state, causing a high level output to appear on terminal 26, which is applied to NAND gate 23. The high level signal is removed from terminal 25. Consequently NAND gate 19 is inhibited, its output signal ceases, and further integration in the summing integrator ceases.

The high level signal at terminal 26 of flip flop 24 is applied to NAND gate 23, along with the vertical synchronization pulse, and NAND gate 23 is caused to operate. As a result driver 27 operates and provides a voltage across its load resistor which is applied to sample and hold circuit 28 as shown in waveform (I). The sample and hold circuit is thus enabled, and receives the voltage level which is stored in summing integrator 29. The output of the sample and hold circuit is applied to digital volt meter 31, and is displayed in a conventional manner.

The signal provided at output 25 of flip flop 24 is shown as waveform (F). It can be seen that during every alternate vertical interval, from the leading edge of the vertical synchronization pulse to the beginning of the next, there is a high level output, while during the intervening periods, the level is low and therefore can be considered as a blanking signal. Integration during the sample period, that is, of the period during which the thermal gradient is present on the screen is achieved during every alternate vertical scan period as shown in waveform (G), and readout is performed during the other vertical scan periods.

Furthermore, during each alternate vertical synchronization pulse period, a high level signal appears at the output of inverter 30 as shown in waveform (H), which signal is provided as a reset signal to the summing integrator, clearing it of the established ramp voltage level.

With the circuit described above, it will be noted that horizontal and vertical synchronization pulses are operated upon to define a scanning field within which the percentage of field determination is provided. Switch 6 selects a particular thermographic gradient signal available from monitor 4, during the time of which a ramp signal is produced. The amplitude of the ramp signal is measured by digital volt meter 31. Since only a fraction of the scanned field results in a ramp voltage, the measured output voltage will of course be a proportion of the entire field.

The voltmeter is set to read numerically 100 in a conventional manner simply by the selection in switch 6 of a terminal which is connected to switch 40. Switch 40 alternatively selects one of the thermographic temperature range signals, or a high logic level (+) for calibration. Upon selection of the calibration level, voltage divider 34 is adjusted, as by variation of a potentiometer as one of its elements, to cause the digital voltmeter 31 to read 100 (or 100%). This simulates a gradient which covers the entire monitor screen. A potentiometer connected to the sample and hold circuit 28 is adjusted when empty of signal (i.e., with no input signal) to cause the digital voltmeter to read zero. Once the adjustment is made, proportions of the scanned field will read on the voltmeter as a percentage fraction.

Of course, switch 40 can be deleted and one of the terminals 5 of switch 6 can be connected to a high level logic signal and be dedicated for calibration purposes.

While the apparatus described above as the preferred embodiment has utilized integration during alternate scan fields, and sampling and display during intervening scan fields, of course it will be seen that this is not specifically necessary. Apparatus can be designed by a person skilled in the art understanding this invention to sample and display during one-half of the vertical synchronization pulse, and reset the summing integrator during the second half. Integration would then occur during each scan period, rather than every alternate scan period. The sampling circuit would of course then hold the sampled voltage level for the period between successive periods, in order that the digital display can provide a readout during that period.

As noted earlier, circuitry can be provided to intensify selected boundaries, i.e. by providing a signal to the video display brightness circuitry during the integration period.

The display need not necessarily be a digital voltmeter 31, but can be some other form of display such as an analog voltmeter, an electronic bar graph etc. Additional integration, sample and hold and four input NAND gates can be connected to the remaining circuitry in parallel, with the input to additional shapers 21 connected to different thermographic gradient signals, the outputs of which can be connected to a bar graph or other electronic graphical display to simultaneously show percentage areas of different temperature ranges. This would allow areas containing particular ranges of signal levels or temperature ranges to be compared.

Where the video display displaying thermographic or other isotherm regions does not provide signals on terminals or at a socket as aforenoted which correspond to various ranges of video signal levels, these can be provided by connecting window comparators set to operate at different voltage spans to the video signal line in video processing circuitry of a video monitor. The window comparators would then provide output signals corresponding to various shades of grey which would correspond to various temperature ranges.

It will be appreciated that the switch 6 could be replaced by a multiplex circuit by which all of the samples are available for readout simultaneously. As an alternative to multiplexing, parallel circuits as described herein could be used, each feeding an output readout circuit or device.

By temporarily selecting a particular isotherm a signal can be fed to the brightness circuitry of the monitor to temporarily brighten circuitry under study which is different from the area measured. In this manner flashing regions or other modes of designating areas can be provided.

By alternately or simultaneously selecting two or more isotherms for processing, for example with a pair of switches 6, operating as boundary control knobs, the circuitry either multiplexed or in parallel can provide for rapid comparative analysis of two sampled areas.

In the preferred embodiment described above, the NAND gates used were type CD4011 available from R.C.A. Corporation. The shaper was type CD4069 from the same source. The operational amplifier in the summing integrator, type AD523 was supplied by Analog Devices Corporation. The transistor used in the summing integrator was Type MPS6521, while the sample and hold circuit used was Type 4856, available from Teledyne Philbrick Corp. The digital voltmeter was Type AD2009 available from Analog Devices. The infrared camera, control unit and display monitor was available as AGA Thermovision System 680, and the colour monitor display which contains a socket which provides signals used for switch 6 is also available from AGA as Type CM7000.

This system can also be used in fields other than medicine. For instance it can be used to give quantified values for heat loss areas from buildings, homes, etc. It can also be used to quantify land regions having different vegetation growth characteristics when used from a high flying apparatus such as a satellite or airplane. Other applications will also be come evident to those skilled in the art understanding this invention.

I claim:

1. An area meter for a video thermographic display having a scan field comprising means for defining a predetermined area within said scan field and means for determining and displaying a numerical representation of a proportional area of said predetermined area relative to the total area of the scan field.

2. A thermographic area meter as defined in claim 1 in which said predetermined area corresponds to regions between predetermined temperature isotherms within a video thermographic scan field.

3. An area meter as in claim 1, further comprising means for adjusting the size of said defined predetermined area.

4. An area meter as in claim 1, further comprising means for adjusting the location of said defined predetermined area relative to said scan field.

5. An area meter for use with video display apparatus forming a video scan field comprising:
   means responsive to received horizontal synchronizing signals used in forming said video scan field for providing a first signal representing the time between said horizontal synchronizing signals;
   means responsive to received vertical synchronizing signals used in forming said video scan field for providing a second signal representing the time between said vertical synchronizing signals;
   means for receiving a plurality of sample slice signals corresponding to various display windows from video display circuitry within said apparatus synchronized with said horizontal and vertical synchronizing signals;
   means for selecting a received slice signal from said plurality of sample slice signals corresponding to a particular image portion of said video scan field and for providing a pulse signal during the period of a selected slice signal; and
   summing integration means responsive to a predetermined coincidence relationship between said first, second and pulse signals for providing as an output an increasing ramp signal which is an integration of a voltage valve during the period between a first pair of received vertical synchronization signals and during the intervals between received horizontal synchronization signals and during the presence of said pulse signal.

6. A thermographic area meter as defined in claim 5 further including means for providing said ramp signal during the intervals between alternate pairs of vertical synchronization signals, means for sampling and storing the highest level ramp signal during the remaining intervals between vertical synchronization signals, and means for displaying the voltage level of the stored ramp signal.

7. An area meter as defined in claim 5 further including means for providing an output signal for effecting video display variations during the period of each selected slice signal.

8. A thermographic area meter as defined in claim 5, further including means for providing said ramp signal during the intervals between pairs of vertical synchronization signals, means for sampling and storing the highest level ramp signal during such interval, and means for displaying the voltage level of the stored ramp signal.

9. A thermographic area meter as defined in claim 5 wherein said voltage value is a constant voltage.

10. A thermographic area meter as defined in claim 1 in which the summing integration means is comprised of a circuit comprising an operational amplifier having an integrating storage capacitor connected between input and output terminals thereof, a semiconductor switch connected across the capacitor, a four input NAND gate connected at its output terminal to an input of said circuit, means connecting the output of said means for selecting to one of the input terminals of the NAND gate, means for applying said first signal to a second input terminal of the NAND gate, means for providing an alternate vertical field blanking signal to the fourth input terminal of the NAND gate, and means for applying reset signals during the vertical synchronization signal period outside the period of the blanking signal to the input of the semiconductor switch to cause discharging of the capacitor whereby its stored voltage and the resulting output signal is returned to zero.

11. A thermographic area meter as defined in claim 10 further including a sample and hold circuit, having a signal input connected to an output of the operational amplifier for storing the output voltage therein, and having an enable input connected to the output of means for applying the alternate vertical field blanking signal for receipt of the blanking signal as an enable signal, and means connected to the output of the sample and hold circuit for displaying the voltage stored therein.

12. A thermographic area meter as defined in claim 11 in which said means for providing said first and second signals each comprises a respective multivibrator means for the received horizontal and vertical signals, each said multivibrator means providing signals corresponding to the time between received synchronization signals but delayed a predetermined time period following the end of a synchronization pulse and extending to a time preceding the beginning of a following synchronization pulse.

13. A thermographic area meter as defined in claim 12 in which the means for displaying is comprised of a digital voltmeter.

14. A thermographic area meter as defined in claim 3 further comprising a voltmeter for displaying the final level of the ramp signal.

15. A thermographic area meter as defined in claim 14 further including a sample and hold circuit for storing the highest level ramp signal voltage during a time period corresponding to the interval between a second pair of vertical synchronization signals immediately following the first pair and for providing the stored voltage to a digital voltmeter.

16. A thermographic area meter as defined in claim 14, further including a sample and hold circuit for storing the highest level ramp signal voltage during a time period immediately following the selection of said slice signals corresponding to said particular portion of the video scan field, and for providing the stored signal voltage to a digital voltmeter.

17. A thermographic area meter as defined in claim 5 in which the summing integration means is comprised of a circuit comprising an operational amplifier having an integrating storage capacitor connected between input and output terminals thereof, a semiconductor switch connected across the capacitor, a NAND gate having at least three inputs connected at its output terminal to an input of said circuit; means connecting the output of said means for selecting to one of the input terminals of the NAND gate, further means for applying signals corresponding to the time between horizontal synchronization signals to a second input terminal of the NAND gate, the vertical synchronization signals to a third input terminal of the NAND gate, and means for applying reset signals during the signal period immediately following the sample and hold pulse period to the input of the semiconductor switch to cause discharging of the capacitor whereby its stored voltage and the resulting output signal is returned to zero.

18. A thermographic area meter as defined in claim 17 further including a sample and hold circuit, having a signal input connected to an output of the operational amplifier for storing the output voltage therein, and having an enable input connected to the output of means for applying the blanking signal as an enable signal, and means connected to the output of the sample and hold circuit for displaying the voltage stored therein.

* * * * *